US00PP31393P2

(12) United States Plant Patent
Hansen

(10) Patent No.: US PP31,393 P2
(45) Date of Patent: Jan. 21, 2020

(54) ***COREOPSIS* PLANT NAMED 'SASSY SAFFRON'**

(50) Latin Name: *Coreopsis verticillata*
Varietal Denomination: Sassy Saffron

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,866

(22) Filed: Jan. 24, 2019

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 5/02
See application file for complete search history.

*Primary Examiner* — Kent L Bell

(57) ABSTRACT

A new and distinct Threadleaf Coreopsis plant, *Coreopsis verticillata* plant named 'Sassy Saffron', with narrowly-linear, deeply-dissected, typically 3 to 6-lobed foliage of bright-green, numerous flowers of rich lemon-yellow ray florets with deep maroon center over a prolonged flowering season from mid-June until late summer. The new plant is useful for landscaping as a specimen plant, en masse, in containers and as a cut flower.

1 Drawing Sheet

Botanical designation: *Coreopsis verticillata.*
Cultivar denomination: 'Sassy Saffron'.

STATEMENT REGARDING PRIOR DISCLOSURES UNDER 37 CFR 1.77(b)(6)

The first public disclosure of the claimed plant, in the form of a website to the public and email release to customers, was made by Walters Gardens, Inc. on Feb. 1, 2018. Walters Gardens, Inc. obtained the new plant and information about the new plant directly from the inventor. No plants of *Coreopsis* 'Sassy Saffron' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct Threadleaf Coreopsis herein also referred to as *Coreopsis* 'Sassy Saffron', by the cultivar name, 'Sassy Saffron', or as the new plant. The new plant was initially selected by the inventor in June of 2016 from a block of seedlings from the cross in the summer of 2014 involving the plant identified by breeder code HK10-2-10 (not patented) crossed with siblings of HK10-2-10 (not patented) in the research facility of a wholesale perennial nursery based in Zeeland, Mich., USA. The single seedling identified by breeder code 14-1-7 was then isolated and compared in subsequent years to other coreopsis and subsequently found to be different from all cultivars known to the discoverer. In the evaluation process the new plant was assigned the breeder code 14-1-7.

Asexual propagation at the same nursery in Zeeland, Mich., USA by cuttings has shown 'Sassy Saffron' to be stable and reproduce true to type in successive generations.

SUMMARY OF THE PLANT

*Coreopsis* 'Sassy Saffron' has not been observed in all possible environmental conditions. The phenotype may vary slightly with changes in environments such as light intensity, fertility, water availability, etc. without, however any variation in genotype.

*Coreopsis* 'Sassy Saffron' is distinct from all cultivars known to the inventor in the following traits:

1. Narrow foliage with compact height and dense habit.
2. Heavy flowering of rich lemon-yellow ray florets with deep maroon centers.
3. Flowers produced tightly and densely above the bright-green thin foliage.
4. Long flowering period beginning with concentration in mid-June and continuing until late summer.

Plants of *Coreopsis* 'Sassy Saffron' are most similar to 'Curry Up' U.S. Plant Pat. No. 28,521, 'Red Hot Vanilla' U.S. Plant Pat. No. 30,909, 'Route 66' U.S. Plant Pat. No. 20,609, 'Electric Avenue' U.S. Plant Pat. No. 24,688, 'Broad Street' U.S. Plant Pat. No. 24,598 and 'Red Chiffon' U.S. Plant Pat. No. 27,528. 'Curry Up' has ray florets that are deeper golden on the outside and lighter reddish in the inside. 'Red Hot Vanilla' has ray florets that are cream-colored on the outside and dark red in the center. 'Route 66' has ray florets that are paler yellow on the outside and lighter reddish in the center with flecking toward apex. 'Electric Avenue' has ray florets that are solid yellow without the dark red center. 'Broad Street' has lighter reddish ray florets with just a speckling of the yellow toward the apices. 'Red Chiffon' has ray florets that are also paler yellow on the outside and not as dark burgundy in the inside, and the flowers produce no seed. The female and exact male parents were not preserved, nor were photographs maintained, thus no comparison between the new plant and the female and male parents is possible.

BRIEF DESCRIPTION OF THE DRAWINGS

The color drawings illustrate the overall characteristics of *Coreopsis* 'Sassy Saffron' as three-year-old plants grown in full-sun in Zeeland, Mich. The colors are as true as reasonably possible given the technology available. The color values may vary slightly depending on light intensity and quality.

DETAILED BOTANICAL DESCRIPTION

Figure 1:
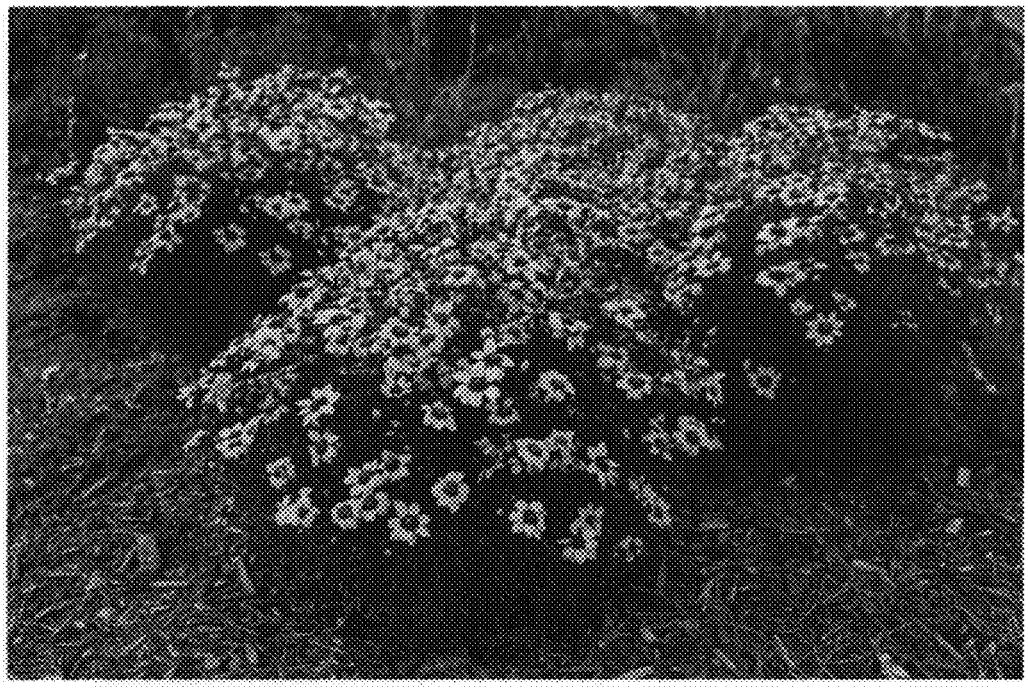
FIG. 1 shows three new plants in a landscape environment.
Figure 2:
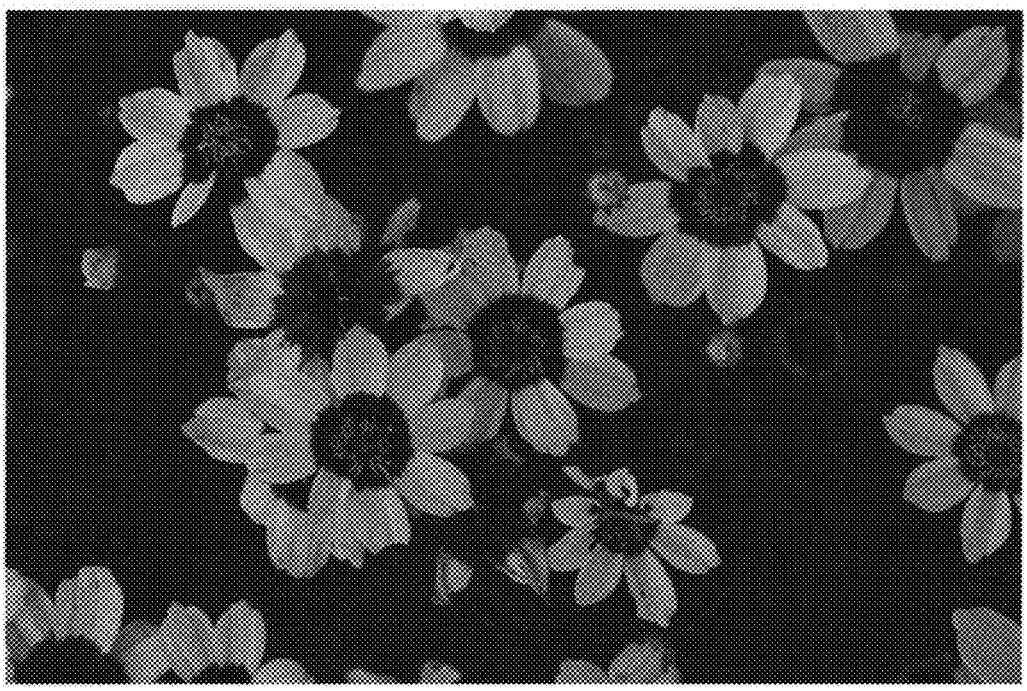
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent HK10-2-10; male or pollen parent was a sibling to HK10-2-10; HK10-2-10 is a proprietary selected seedling of 'Route 66' times itself;

Asexual propagation: Cuttings, about 10 to 14 days to initiate roots; time to finish as #1 field grown size about 9 months;

Plant habit: Dense axillary branches; rounded, herbaceous perennial mound; up to 55.0 cm wide and 42.0 cm tall; average about 53.0 cm across and 40.0 cm tall;

Branches: Up to 12 per stem, lower branches compound; glabrous, cylindrical; to 19.5 cm long and 2.0 mm diameter; emerging at an angle about 55 degrees above horizontal; internode length average about 3.5 cm; color nearest RHS 146B; two leaves per node;

Leaves: Opposite, entire, glabrous; deeply dissected, irregularly lobed; typically tri-lobed, acute apex; base attenuate; sessile; up to 5.0 cm long and 5.5 mm wide, average about 4.1 cm long and 3.8 cm wide; side lobes at about a 60° angle to center lobe, to 26.0 mm long and 2.0 mm across; center lobe to 38.0 mm long and 3.0 mm wide;

Leaf color: Young expanding leaves adaxial nearest RHS 137B and abaxial nearest RHS 137C; mature leaves adaxial nearest RHS 137A, abaxial nearest RHS 137B;

Veins: Pinnate; only abaxial midvein obvious;

Abaxial midveins color: Nearest RHS 137B;

Inflorescence: Radiate; composite consisting of ray and disk florets; on terminal branches; about 3.5 cm diameter, about 1.2 cm tall from lower involucral bracts to top of disk florets; attitude upright to outwardly; to about 100 inflorescences per stem;

Flower fragrance: Not detected;

Phyllary: Two distinct whorls, outer or lower set consisting of about nine, acute apex, lanceolate, truncate base, glabrous, to about 3.5 mm long and 2.0 mm wide at base; inner or upper set tight against ray florets, usually eight in number, to about 4.5 mm long and about 3.0 mm wide, deltoid to ovate; acute apex and truncate base;

Phyllary color: Lower set between RHS 137B and RHS 137A on both surfaces with lighter margin of nearest RHS 160B; upper set nearest RHS 137B in proximal and central portion of both abaxial and adaxial, marginally and distally nearest RHS 153D in both sides;

Flowering period: Early summer until late summer, for about 10 weeks; producing over 40 flowers per stem and over 200 flowers per plant;

Flower longevity: 4 to 6 days on the plant or as a cut flower;

Flower buds: One to two days before showing ray floret color spherical with slightly flattened top, 4.0 mm wide and 5.0 mm tall;

Flower bud color: Nearest RHS 15B;

Peduncle: Cylindrical; glaucous, thin, wiry, upright attitude, strong, many branched; to about 4.0 mm wide at base and about 30.0 cm long before flowers; about seven nodes, average internode spacing about 4.3 cm; spacing about 1.5 cm proximally and to about 5.0 cm in the central portion; nodes same color as surround stem;

Peduncle color: Between RHS 137A and RHS 137B;

Pedicel: Cylindrical; glaucous, thin, wiry, strong; to about 1.0 mm in diameter, 5.5 cm long;

Pedicel color: Nearest RHS 137B;

Ray florets: Imperfect; staminate; zygomorphic;

Ray florets: Ligule; typically 8 per inflorescence; oblong elongate, glabrous; apex typically two-notched, margin entire; base claw, narrowly cuneate to attenuate; opening flat to form 180° angle with other ray florets; parallel veined; glabrous adaxial and adaxial; about 1.3 cm long and about 8.0 mm wide; basal corolla tube about 1.5 mm to 2.5 mm long and about 0.7 mm diameter; containing only gynoecium with style about 3.0 mm long and bifid stigma;

Ray floret color: Adaxial basal 4.0 mm nearest RHS 187A, distal 9.0 mm nearest RHS 3A; abaxial basal 4.0 mm nearest RHS 5B with undertone of nearest RHS 187A, distal 9.0 mm nearest RHS 5B;

Style color: Of ray floret nearest RHS 15B;

Stigma color: Of ray floret nearest RHS 15A;

Disk Florets: About 34 per capitulum; consisting of tepals, staminal tube and pistil; size about 6.0 mm long by 1.0 mm wide at top and about 0.7 mm diameter at base;

*Tepals.*—Five; 2.5 mm long and 1 mm wide, corolla fused in the basal 2.0 mm, acute apex.

*Tepal color.*—Adaxial and abaxial nearest RHS 7A.

*Staminal tube.*—Made up of five fused stamens, about 3.0 mm long.

*Anther.*—About 1 mm long, nearest RHS 166A.

*Pollen.*—Fine, round, closest to RHS 15A.

*Style.*—About 4.0 mm long; nearest RHS 15B.

*Stigma.*—Bifid and cochleate as it matures; color nearest RHS 15A.

Seed: Linear, flattened, slightly arcuate; with rounded apex and rounded base; margins microerose; about 5.0 mm long, about 2.5 mm across in middle and about 0.5 mm thick;

Seed color: Variable, between RHS 200A and RHS 202A;

*Coreopsis verticillata* 'Sassy Saffron' is tolerant of winter temperatures as low as −20° C. and summer temperatures as high as 40° C. Once established it is also tolerant of dry summer conditions but does best with ample moisture and good drainage. It is not known to be tolerant of diseases and pest that are common to other *Coreopsis* cultivars.

I claim:

1. A new and distinct cultivar of *Coreopsis* plant named 'Sassy Saffron' as described and illustrated.

* * * * *